(12) United States Patent
Wierzbicki et al.

(10) Patent No.: US 6,844,445 B2
(45) Date of Patent: Jan. 18, 2005

(54) INDENOINDOLONE COMPOUNDS

(75) Inventors: Michel Wierzbicki, L'etang la Ville (FR); Marie-Françoise Boussard, Mareil sur Mauldre (FR); Anne Rousseau, Longjumeau (FR); Jean Albert Boutin, Suresnes (FR); Philippe Delagrange, Issy les Moulineaux (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 1 day.

(21) Appl. No.: 10/100,784

(22) Filed: Mar. 19, 2002

(65) Prior Publication Data

US 2002/0173531 A1 Nov. 21, 2002

(30) Foreign Application Priority Data

Mar. 19, 2001 (FR) ............................................. 01 03667

(51) Int. Cl.[7] .................. C07D 207/323; C07D 207/36; A61K 31/403
(52) U.S. Cl. ....................................... 548/420; 514/410
(58) Field of Search ........................... 548/420; 514/410

(56) References Cited

PUBLICATIONS

FDA mulls drug to slow late–stage Alzheimer's [online], [retrieved on Sep. 24, 2003]. Retrieved from the Internet<URL:http://www.cnn.com/2003/HEALTH/conditions/09/24/alzheimers.drug.ap/index.html>.*
Lala et al., Role of nitric oxide in tumor progression: Lessons from experimental tumors, Cancer and Metastasis Reviews, Kluwer Academic Publishers, 1998 17(1), 91–106.*
Hamrs et al. Melatonin is protective in necrotic but not in caspase–dependent, free radical–independent apoptotic neuronal cell death in primary neuronal cultures, FASEB Journal (2000), 14(12), 1814–1824.*
Kevin et al., The coupling reactions of 3–acylindoles and proof of structure of the palladium(II) acetate mediated cyclization reaction product of 3–benzoyl–1–methylindole, Heterocycles (1983), 20(12), 2433–6.*
Li, et al., *Drugs of the Future*, 2000, 25 (9), 945–957.
Krause, et al., *Society for Neuroscience*, 1996, 22, No. 551.19, 1400.
Vacas, et al., *J. Pineal Res.*, 1992, 13, 60–65.
Cagnacci, et al., *J. Pineal Res.*, 1997, 22, 16–19.
Lagneux, et al., *Life Sciences*, 2000, 66 (6), 503–509.
Brydon, et al., *Endocrinology*, 2001, 142 (10), 4264–4271.
Bylesjö, et al., *International Journal of Eating Disorders*, 1996, 20 (4), 443–446.
Ferrari, et al., *Biol. Psychiatry*, 1990, 27, 1007–1020.
Mazzucchelli, et al., *Molecular Brain Research*, 1996, 39, 117–126.
Brown, *CNS Drugs*, 1995, 3 (3), 209–226.
Waldhauser, et al., *Psychopharmacology*, 1990, 100, 222–226.

Skene, et al., *Brain Research*, 1990, 528, 170–174.
Monteleone, et al., *Schizophrenia Research*, 1992, 7, 77–84.
Erlich, et al., *J. Neurosurg.*, 1985, 63, 321–341.
Maurizi, *Medical Hypotheses*, 1988, 27, 271–276.
Kopp, et al., *Behavioural Pharmacology*, 1999, 10, 73–83.
Kopp, et al., *Neuropharmacology*, 2000, 39, 1865–1871.
Rasmussen, et al., *Endocrinology*, 1999, 140 (2), 1009–1012.
Armstrong, et al., *Medical Hypotheses*, 1991, 34, 300–309.
O'Brien, et al., *Clinical Endocrinology*, 1986, 24, 359–364.
Motilva, et al., *Current Pharmaceutical Design*, 2001, 7, 909–931.
Tamarkin, et al., *Science*, 1985, 227, 714–720.
Chemineau, et al., *Rec. Med. Vet.*, 1991, 167 (3/4), 227–239.
Xu, et al., *Drug Development Research*, 1996, 39, 167–173.
Régrigny, et al., *Am. J. Physiol.*, 1998, 275, 139–144.
Stankov, et al., *Neuroscience*, 1993, 52 (2), 459–468.
Leone, et al., *Cephalalgia*, 1996, 16, 494–496.
Brun, et al., *Cephalalgia*, 1995, 15, 136–139.
Ying, et al., *Eur. J. of Pharmacology*, 1993, 246, 89–96.
Laudon, et al., *Journal of Clinical Endocrinology and Metabolism*, 1996, 81 (4), 1336–1342.
Lissoni, et al., *British Journal of Cancer*, 1996, 74, 1466–1468.

* cited by examiner

*Primary Examiner*—Joseph K. McKane
*Assistant Examiner*—Rebecca Anderson
(74) *Attorney, Agent, or Firm*—The Firm of Hueschen and Sage

(57) ABSTRACT

Compound of formula (I):

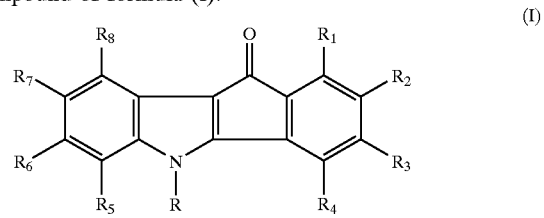

wherein:
R represents hydrogen or a group selected from alkenyl and optionally substituted alkyl,
each of $R_1$ to $R_8$, which may be identical or different, represents hydrogen or a group selected from alkyl, alkenyl, hydroxy, alkoxy, alkenyloxy, arylalkyl, arylalkoxy, carboxy, acyloxy and arylcarbonyloxy,
or one of $R_1$ to $R_8$ forms with an adjacent one $R_1$ to $R_8$ an alkylenedioxy group,
its optical isomers when they exist, and addition salts thereof with a pharmaceutically acceptable acid or base,
with the proviso that:
when R does not represent hydrogen, then at least one of $R_1$ to $R_8$ represents hydroxy or acyloxy,
and the compounds of formula (I) are other than indeno[1,2-b]indol-10(5H)-one and medicinal products containing the same which are useful for treatment of disorders of the melatoninergic system.

6 Claims, No Drawings

INDENOINDOLONE COMPOUNDS

The present invention relates to new indenoindolone compounds.

DESCRIPTION OF THE PRIOR ART

Some indenoindolone compounds have been described in the literature, for example in J. Chem. Soc. Perkin Trans. I 1974, 13, 1523–1525, without any pharmacological activity having been described for those compounds.

The compounds of the present invention are new and have very valuable pharmacological characteristics in respect of melatoninergic receptors.

BACKGROUND OF THE INVENTION

Numerous studies in the last ten years have demonstrated the key role of melatonin (N-acetyl-5-methoxytryptamine) in many physiopathological phenomena and in the control of the circadian rhythm. Its half-life is quite short, however, owing to the fact that it is rapidly metabolised. Great interest therefore lies in the possibility of providing the clinician with melatonin analogues that are metabolically more stable, have an agonist or antagonist character and may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223), as well as for the treatment of Parkinson's disease (J. Neurosurg. 1985, 63, pp. .321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97.04094). It has been possible, for various species, including mammals, for some of those receptors to be located and characterised. In order to be able to understand the physiological functions of those receptors better, it is of great advantage to have available specific ligands. Moreover, such compounds, by interacting selectively with one or other of those receptors, may be excellent medicaments for the clinician in the treatment of pathologies associated with the melatoninergic system, some of which have been mentioned above.

DETAILED DESCRIPTION OF THE INVENTION

In addition to being new, the compounds of the present invention exhibit a strong affinity for melatonin receptors and a significant selectivity for $MT_3$-type sites.

More especially, the present invention relates to compounds of formula (I):

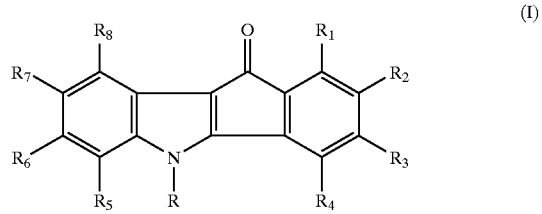

wherein:
R represents a hydrogen atom or a linear or branched ($C_1$–$C_6$)alkenyl or linear or branched ($C_1$–$C_6$)alkyl group optionally substituted by a carboxy group or by a group of formula —$NR_aR_b$ wherein each of $R_a$ and $R_b$, which may be identical or different, represents a hydrogen atom or a linear or branched ($C_1$–$C_6$)alkyl group, or form together with the nitrogen atom carrying them a nitrogen-containing heterocycle, each of $R_1$, $R_2$, $R_3$, $R_4$, $R_5$, $R6$, $R_7$ and $R_8$, which may be identical or different, represents a hydrogen atom or a linear or branched ($C_1$–$C_6$)alkyl group, a linear or branched ($C_1$–$C_6$)alkenyl group, a hydroxy group, a linear or branched ($C_1$–$C_6$)alkoxy group, a linear or branched ($C_1$–$C_6$)alkenyloxy group, an aryl-($C_1$–$C_6$)alkyl group in which the alkyl moiety is linear or branched, an aryl-($C_1$–$C_6$)alkoxy group in which the alkoxy moiety is linear or branched, a carboxy group, a linear or branched ($C_1$–$C_6$)-acyloxy group, or an arylcarbonyloxy group, or one of the groups $R_1$ to $R_8$ forms with an adjacent one of the groups $R_1$ to $R_8$ a ($C_1$–$C_2$)alkylenedioxy group, their optical isomers when they exist, and addition salts thereof with a pharmaceutically acceptable acid or base, with the proviso that:

when R does not represent a hydrogen atom, then at least one of the groups $R_1$ to $R_8$ represents a hydroxy group or a linear or branched ($C_1$–$C_6$)acyloxy group, and the compounds of formula (I) are other than indeno [1,2-b]indol-10(5H)-one.

The term "aryl group" is understood to mean "phenyl", "biphenylyl", "naphthyl" or "tetrahydronaphthyl", each of those groups being optionally substituted by one or more identical or different atoms or groups selected from halogen atoms and linear or branched ($C_1$–$C_6$)alkyl groups, hydroxy groups, linear or branched ($C_1$–$C_6$)alkoxy groups, linear or branched ($C_1$–$C_6$)polyhaloalkyl groups, amino groups (optionally substituted by one or more linear or branched ($C_1$–$C_6$)alkyl groups), nitro groups, linear or branched ($C_1$–$C_6$)acyl groups and ($C_1$–$C_2$)alkylenedioxy groups.

The term "nitrogen-containing heterocycle" is understood to mean a saturated monocyclic group having from 5 to 7 ring members and containing one, two or three hetero atoms, one of those hetero atoms being a nitrogen atom, and the additional hetero atom(s) optionally present being selected from the atoms oxygen, nitrogen and sulphur. Preferred nitrogen-containing heterocycles are the groups pyrrolidinyl, piperidyl, morpholinyl and piperazinyl.

Among the pharmaceutically acceptable acids there may be mentioned by way of non-limiting example hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Among the pharmaceutically acceptable bases there may be mentioned by way of non-limiting example sodium hydroxide, potassium hydroxide, triethylamine, tert-butylamine, etc.

The invention relates also to a process for the preparation of compounds of formula (I), characterised in that a compound of formula (II)

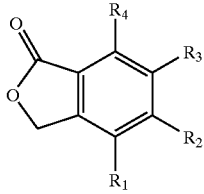
(II)

wherein $R_1$, $R_2$, $R_3$ and $R_4$ are as defined for formula (I), is reacted with N-bromosuccinimide to yield a compound of formula (III):

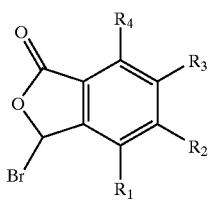
(III)

wherein $R_1$, $R_2$, $R_3$ and $R_4$ are as defined hereinbefore, which is reacted with triphenylphosphine to yield a compound of formula (IV):

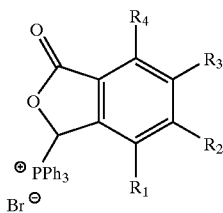
(IV)

wherein $R_1$, $R_2$, $R_3$ and $R_4$ are as defined hereinbefore, which is reacted with a compound of formula (V):

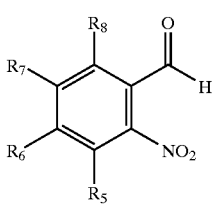
(V)

wherein $R_5$, $R_6$, $R_7$ and $R_8$ are as defined for formula (I), to yield a compound of formula (VI):

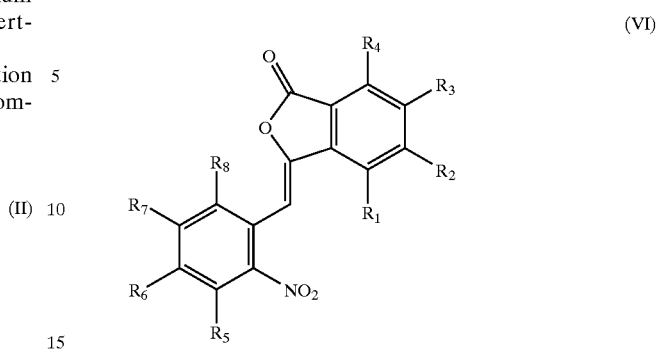
(VI)

wherein $R_1$, $R_2$, $R_3$, $R_4$, $R_5$, $R_6$, $R_7$ and $R_8$ are as defined hereinbefore, which is treated with a base to yield a compound of formula (VII):

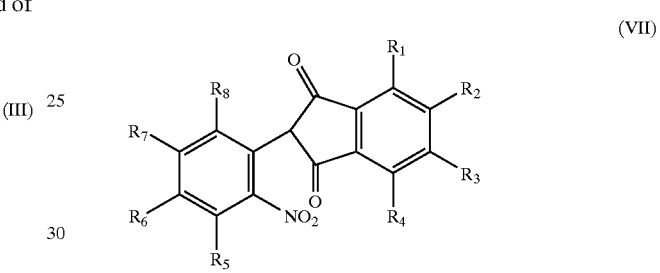
(VII)

wherein $R_1$, $R_2$, $R_3$, $R_4$, $R_5$, $R_6$, $R_7$ and $R_8$ are as defined hereinbefore, which is subjected to the action of a reducing agent to yield, after separation of the isomers where necessary, a compound of formula (Ia), a particular case of the compounds of formula (I):

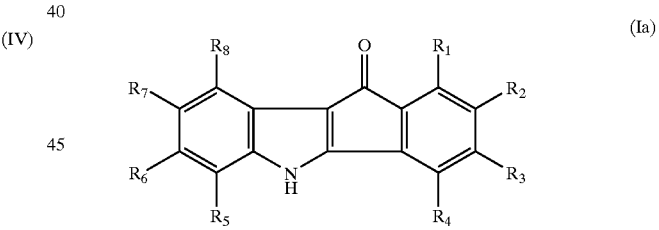
(Ia)

wherein $R_1$, $R_2$, $R_3$, $R_4$, $R_5$, $R_6$, $R_7$ and $R_8$ are as defined hereinbefore, which is reacted, if desired, with a compound of formula (VIII):

R'—Z  (VIII)

wherein R' represents a linear or branched $(C_1-C_6)$alkenyl or linear or branched $(C_1-C_6)$alkyl group each optionally substituted by a carboxy group or by a group of formula —$NR_aR_b$ wherein each of $R_a$ and $R_b$, which may be identical or different, represents a hydrogen atom or a linear or branched $(C_1-C_6)$alkyl group, or form together with the nitrogen atom carrying them a nitrogen-containing heterocycle, and Z represents a leaving group, such as, for example, a halogen atom or a mesylate, tosylate or trifluoromethanesulphonate group, to yield a compound of formula (Ib), a particular case of the compounds of formula (I).

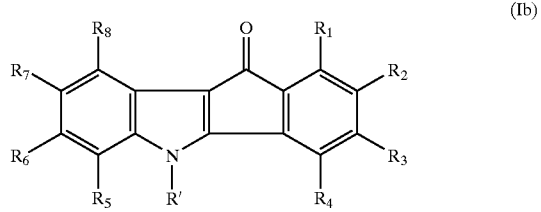

wherein $R_1$, $R_2$, $R_3$, $R_4$, $R_5$, $R_6$, $R_7$, $R_8$ and R' are as defined hereinbefore,
which compounds of formulae (Ia) and (Ib) constitute the totality of the compounds of formula (I), which are purified, if necessary, in accordance with a conventional purification technique, are separated, where appropriate, into their isomers in accordance with a conventional separation technique, and converted, if desired, into addition salts thereof with a pharmaceutically acceptable acid or base.

The compounds of formula (I) wherein one of the groups $R_1$ to $R_8$ represents a hydroxy group may also be obtained by catalytic hydrogenation of the corresponding benzyl ethers or by demethylation of the corresponding methyl ethers.

The compounds of the invention and the pharmaceutical compositions containing them have proved to be useful in the treatment of disorders of the melatoninergic system.

Pharmacological study of the compounds of the invention has in fact demonstrated that they are atoxic, have a high selective affinity for melatonin receptors and have substantial activity on the central nervous system and, in particular, therapeutic properties in respect of sleep disorders, anxiolytic, antipsychotic and analgesic properties, as well as properties in respect of microcirculation, have been found, enabling it to be established that the compounds of the invention are useful in the treatment of stress, sleep disorders, anxiety, seasonal affective disorder, cardiovascular pathologies, pathologies of the digestive system, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, have ovulation-inhibiting and immunomodulating properties and are capable of being used in the treatment of cancers.

The compounds will preferably be used in the treatment of seasonal affective disorder, sleep disorders, cardiovascular pathologies, insomnia and fatigue due to jetlag, appetite disorders and obesity. For example, the compounds will be used in the treatment of seasonal affective disorder and sleep disorders.

The present invention relates also to pharmaceutical compositions comprising a compound of formula (I) in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration, and especially tablets or dragées, sublingual tablets, sachets, parquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, and any associated treatments and ranges from 0.01 mg to 1 g per 24 hours in one or more administrations.

The following Examples illustrate the invention but do not limit it in any way.

The starting materials used are known products or are prepared according to known procedures.

The structures of the compounds described in the Examples were determined according to the usual spectrometric techniques (infrared, NMR, mass spectrometry).

EXAMPLE 1

8-Benzyloxy-2,3dimethoxyindeno[1,2-b]indol-10(5H)-one

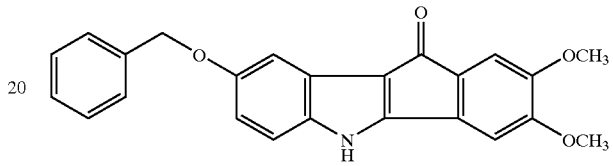

Step A: 3-Bromo-5,6-dimethoxy-phthalide 12 mmol of N-bromosuccinimide are added to 10 mmol of 5,6-dimethoxy-phthalide dissolved in dichloromethane, and then the reaction mixture, lit by a halogen lamp, is refluxed for 5 hours. The mixture is then returned to room temperature and filtered, and the filtrate is evaporated, toluene is added, the resulting suspension is filtered and the filtrate is evaporated. The resulting residue is filtered over silica to yield the expected product.

Step B: (5,6-Dimethoxy-phthalidyl)-triphenylphosphonium bromide 10 mmol of triphenylphosphine are added to 10 mmol of the compound obtained in the preceding Step dissolved in toluene, and then the reaction mixture is refluxed for 3 hours. After returning to room temperature, the mixture is filtered and then the resulting cake is washed and dried to yield the expected product.

Melting point: >260° C.

Step C: 3-(5-Benzyloxy-2-nitro-benzylidene)-5,6-dimethoxy-phthalide

To 10 mmol of 5-benzyloxy-2-nitro-benzaldehyde dissolved in dimethylformamide there are added 10 mmol of triethylamine, and then, in portions, 10 mmol of the compound obtained in the preceding Step. The reaction mixture is then heated at 50° C. for 1 hour 30 minutes, and then returned to room temperature and evaporated. Ether is then added, and the mixture is stirred overnight and then filtered. The resulting cake is then washed to yield the expected product.

Melting point: 170° C.

Step D: 2-(5-Benzyloxy-2-nitrophenyl)-3-hydroxy-5,6-dimethoxy-1H-inden-1-one 10 ml of a 4N sodium hydoxide solution are added to 10 mmol of the compound obtained in the preceding Step dissolved in methanol. The mixture is then heated at 40° C. for 1 hour, and then cooled to 0° C. and brought to pH=1 with a 4N hydrochloric acid solution (12 ml). After stirring overnight at room temperature, the white precipitate that has formed is filtered off, washed and then dried and purified by chromatography over a silica column (eluant:dichloromethane/methanol 99/1) to yield the expected product.

Melting point: 120° C.

Step E: 8-Benzyloxy-2,3-dimethoxyindeno[1,2-b]indol-10 (5H)-one

A solution of the compound obtained in the preceding Step (10 mmol) in dimethyl-formamide is placed under hydrogen in the presence of Raney nickel. After removal of the catalyst by filtration, the solvent is removed by evaporation and the residue is dried to yield the expected product.

Melting point 235° C.

EXAMPLE 2

2,3-Dimethoxy-8-hydroxy-indeno[1,2-b]indol-10(5H)-one

To a solution of the compound described in Example 1 (10 mmol) in a mixture of methanol/dimethylformamide 70/30 there are added 20 mmol of a 1N sodium hydroxide solution and then 1 g of 10% palladium-on-carbon. The mixture is then placed under a hydrogen pressure of 80 mbars for 2 hours at room temperature, and then the catalyst is filtered off, a solution of 1N hydrochloric acid (20 ml) is added to the filtrate, and the solvents are removed by evaporation. The resulting residue is then taken up in isopropanol, and the the resulting suspension is filtered, the filtrate is evaporated and the resulting residue is washed to yield the expected product.

Melting point: >260° C.

EXAMPLE 3

2,3-Dimethoxy-8-hydroxy-5-methyl-indeno[1,2-b]indol-10 (5)-one

To a solution of the compound described in Example 2 (10 mmol) in dimethylformamide there are added 11 mmol of potassium carbonate, and then the reaction mixture is brought to 90° C. and 11 mmol of iodomethane are added. The reaction mixture is then maintained at 60° C. for 1 night, and the solvent is then removed by evaporation, water is added and the resulting suspension is filtered. The cake is then recrystallised from ethanol to yield the expected product.

Melting point: 241° C.
Elemental microanalysis

|  | C % | H % | N % |
|---|---|---|---|
| calculated | 68.89 | 4.89 | 4.53 |
| found | 69.04 | 4.81 | 4.61 |

EXAMPLE 4

7-Benzyloxy-8-methoxy-ideno[1,2-b]indol10(5H)-one

The expected product is obtained according to the process described in Example 1 starting from phthalide and 4-benzyloxy-5-methoxy-2-nitro-benzaldehyde.

EXAMPLE 5

7-Hydroxy-8-methoxy-indeno[1,2-b]indol-10(5H)-one

The expected product is obtained according to the process described in Example 2 starting from the compound described in Example 4.

Melting point >260° C.
Elemental microanalysis:

|  | C % | H % | N % |
|---|---|---|---|
| calculated | 72.45 | 4.18 | 5.28 |
| found | 72.20 | 4.06 | 5.31 |

EXAMPLE 6

8-Benzyloxy-1,4-dimethoxyindeno[1,2-b]indol-10(5H)-one

The expected product is obtained according to the process described in Example 1 starting from 4,7-dimethoxy-phthalide and 5-benzyloxy-2-nitro-benzaldehyde.

EXAMPLE 7

1,4-Dimethoxy-8-hydroxy-indeno[1,2-b]indol-10(5H)-one

The expected product is obtained according to the process described in Example 2 starting from the compound described in Example 6.

Melting point: >260° C.

EXAMPLE 8

1,4-Dimethoxy-8-hydroxy-5-methyl-indeno[1,2-b]indol-10 (5H)-one

The expected product is obtained according to the process described in Example 3 starting from the compound described in Example 7.

EXAMPLE 9

8-Benzyloxy-1-hydroxy4-methoxy-indeno[1,2-b]indol-10 (5H)-one

The expected product is obtained by selective demethylation of the compound described in Example 6, according to the process described in Tet. 1996, 52 (43), 13623–640.

EXAMPLE 10

1,8-Dihydroxy-4-methoxy-indeno[1,2-b]indol-10(5H)-one

The expected product is obtained according to the process described in Example 2 starting from the compound described in Example 9.

EXAMPLE 11

2,3-Dimethoxy-indenol[1,2-b]indol-10(5H)-one

The expected product is obtained according to the process described in Example 1 starting from 5,6-dimethoxy-phthalide and 2-nitro-benzaldehyde.

Melting point 260° C.

EXAMPLE 12

2,3-Dimethoxy-7,8methylenedioxy-indeno[1,2-b]indol-10 (5H)-one

The expected product is obtained according to the process described in Example 1 starting from 5,6-dimethoxy-phthalide and 4,5-methylenedioxy-2-nitro-benzaldehyde.

EXAMPLE 13

7,8-Methylenedioxy-indeno[1,2-b]indol-10(5H)-one

The expected product is obtained according to the process described in Example 1 starting from phthalide and 4,5-methylenedioxy-2-nitro-benzaldehyde.

EXAMPLE 14

8-Benzyloxy-1,3-dimethoxy-indeno[1,2-b]indol-10(5H)-one

By proceeding in accordance with the process described in Example 1 starting from 4,6-dimethoxy-phthalide and 5-benzyloxy-2-nitro-benzaldehyde, the expected product is obtained in a mixture with 8-benzyloxy-2,4-dimethoxy-indeno[1,2-b]indol-10(5H)-one.

The expected product is obtained by separating the mixture by chromatography over a silica column (eluant: dichloromethane/methanol 98/2), and evaporating the second fraction eluted.

EXAMPLE 15
1,3-Dimethoxy-8-hydroxy-indeno[1,2-b]indol-10(5H)-one

The expected product is obtained according to the process described in Example 2 starting from the compound described in Example 14.

EXAMPLE 16
8-Benzyloxy-2,4dimethoxy-indeno[1,2-b]indol-10(5H)-one

By proceeding in accordance with the process described in Example 1 starting from 4,6-dimethoxy-phthalide and 5-benzyloxy-2-nitro-benzaldehyde, the expected product is obtained in a mixture with 8-benzyloxy-1,3-dimethoxy-indeno[1,2-b]indol-10(5H)-one.

The expected product is obtained by separating the mixture by chromatography over a silica column (eluant:dichloromethane/methanol 98/2), and evaporating the first fraction eluted.

EXAMPLE 17
2,4-Dimethoxy-8-hydroxy-indeno[1,2-b]indol-10(5H)-one

The expected product is obtained according to the process described in Example 2 starting from the compound described in Example 16.

EXAMPLE 18
5-Allyl-2,3-dimethoxy-8-hydroxy-indeno[1,2-b]indol-10(5H)-one

The expected product is obtained according to the process described in Example 3 starting from the compound described in Example 2, replacing iodomethane by allyl bromide.

EXAMPLE 19
1,3-Dimethoxy-5-(2-dimethylaminoethyl)-8-hydroxy-indenol[1,2-b]indol-10(5H)-one The expected product is obtained according to the process described in Example 3 starting from the compound described in Example 15, replacing iodomethane by 2-chloro-N,N-dimethylethanamine.

EXAMPLE 20
1,4-Dimethoxy-5(2-dimethylaminoethyl)8-hydroxy-indeno[1,2-b]-indol-10(5H)-one The expected product is obtained according to the process described in Example 3 starting from the compound described in Example 7, replacing iodomethane by 2chloro-N,N-dimethylethanamine.

EXAMPLE 21
2,3-Dimethoxy-5-(2-dimethylaminoethyl)-8-hydroxy-indeno[1,2-b]-indol-10(5H)-one The expected product is obtained according to the process described in Example 3 starting from the compound described in Example 2, replacing iodomethane by 2-chloro-N,N-dimethylethanamine.

Melting point: 216° C.
Elemental microanalysis:

|            | C %   | H %  | N %  |
|------------|-------|------|------|
| calculated | 68.84 | 6.05 | 7.65 |
| found      | 68.64 | 5.98 | 7.58 |

EXAMPLE 22
2,3-Dimethoxy-8-hydroxy-5-[2-(4-morpholinyl)-ethyl]-indeno[1,2-b]-indol-10(5H)-one The expected product is obtained according to the process described in Example 3 starting from the compound described in Example 2, replacing iodomethane by 4-(2-chloroethyl)-morpholine.

Melting point: 228–232° C.
Elemental microanalysis:

|            | C %   | H %  | N %  |
|------------|-------|------|------|
| calculated | 67.63 | 5.92 | 6.86 |
| found      | 67.19 | 5.93 | 6.80 |

EXAMPLE 23
2,3,8-Trimethoxy-indeno[1,2-b]indol-10(5H)-one

The expected product is obtained according to the process described in Example 1, replacing 5-benzyloxy-2-nitro-benzaldehyde by 5-methoxy-2-nitrobenzaldehyde.

EXAMPLE 24
(8-Hydroxy-2,3-dimethoxy-10-oxoindeno[1,2-b]indol-5(10H)-yl)acetic acid sodium salt:

step A: Methyl (8-hydroxy-2,3-dimethoxy-10-oxoindeno[1,2-b]indol-5(10H)-yl)acetate The expected product is obtained according to the process described in Example 3 starting from the compound described in Example 2, replacing iodomethane by methyl chloroacetate.

Step B: (8-Hydroxy-2,3-dimethoxy-10-oxoindeno[1,2-b]indol-5(10H)-yl)acetic acid sodium salt:

The expected product is obtained by hydrolysis of the ester obtained in the preceding Step A with sodium hydroxide.

Melting point: >260° C.
Elemental microanalysis:

|            | C %   | H %  | N %  |
|------------|-------|------|------|
| calculated | 60.80 | 3.76 | 3.73 |
| found      | 60.38 | 3.77 | 3.74 |

Pharmacological Study of the Compounds of the Invention

EXAMPLE 25
Study of Binding to Melatonin $MT_3$ Binding Sites

Binding to $MT_3$ sites is characterised by remarkably rapid association and disassociation kinetics and by tissue localisation (brain).

The binding experiments on $MT_3$ sites are carried out on hamster brain membranes using 2-[$^{125}$I]iodomelatonin as radioligand in accordance with the protocol described by P. Paul et al. (J. Pharmacol. Exp. Ther. 1999, 290, 334). The membranes are incubated for 30 minutes with 2-[$^{125}$I] iodomelatonin at a temperature of 4° C. and different concentrations of the test compounds. After incubation, the membranes are rapidly filtered and then washed with cold buffer using a filtration system. The fixed radioactivity is measured using a scintillation counter.

The $IC_{50}$ values found for the compounds of the invention indicate a strong affinity for $MT_3$-type sites, those values being from 0.2 to 100 nM. By way of comparison, melatonin has an $IC_{50}$ of 45 nM in this test.

EXAMPLE 26
Pharmaceutical Composition

| Formulation for the preparation of 1000 tablets each containing 10 mg of active ingredient | |
| --- | --- |
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

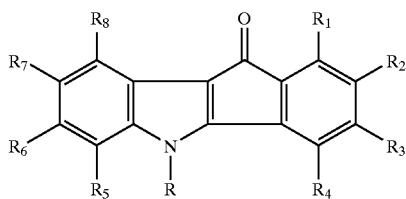

wherein:
R represents hydrogen, linear or branched ($C_1$–$C_6$)alkenyl or linear or branched ($C_1$–$C_6$)alkyl optionally substituted by carboxy or by a group of formula —$NR_aR_b$ wherein each of $R_a$ and $R_b$, which may be identical or different, represents hydrogen or linear or branched ($C_1$–$C_6$)alkyl, each of $R_1$, $R_2$, $R_3$, $R_4$, $R_5$, $R_6$, $R_7$ and $R_8$, which may be identical or different, represents hydrogen, linear or branched ($C_1$–$C_6$)alkyl, linear or branched ($C_1$–$C_6$)alkenyl, hydroxy, linear or branched ($C_1$–$C_6$)alkoxy, linear or branched ($C_1$–$C_6$)alkenyloxy, aryl-($C_1$–$C_6$)alkyl in which the alkyl moiety is linear or branched, aryl-($C_1$–$C_6$)alkoxy in which the alkoxy moiety is linear or branched, carboxy, linear or branched ($C_1$–$C_6$)-acyloxy, or arylcarbonyloxy, its optical isomers, and addition salts thereof with a pharmaceutically acceptable acid or base, with the proviso that:

when R does not represent hydrogen, then at least one of $R_1$ to $R_8$ represents hydroxy or linear or branched ($C_1$–$C_6$)acyloxy, and the compounds of formula (I) are other than indeno[1,2-b]indol-10(5H)-one, it being understood that the term "aryl" is "phenyl", "biphenylyl", "naphthyl" or "tetrahydronaphthyl", each of those groups being optionally substituted by one or more identical or different atoms or groups selected from halogen, linear or branched ($C_1$–$C_6$)alkyl, hydroxy, linear or branched ($C_1$–$C_6$)alkoxy, linear or branched ($C_1$–$C_6$)polyhaloalkyl, amino (optionally substituted by one or more linear or branched ($C_1$–$C_6$)alkyl), nitro, linear or branched ($C_1$–$C_6$) acyl and ($C_1$–$C_2$)alkylenedioxy.

2. A compound of claim 1 which is 2,3-dimethoxy-8-hydroxy-5-methyl-indeno[1,2-b]indol-10(5H)-one.

3. A compound of claim 1 which is 2,4-dimethoxy-8-hydroxy-indeno[1,2-b]indol-10(5H)-one.

4. A compound of claim 1 which is 2,3-dimethoxy-5-(2-dimethylaminoethyl)-8-hydroxy-indeno[1,2-b]indol-10(5H)-one.

5. A method for treating a living animal body afflicted with a condition selected from sleep disorders, stress, anxiety, seasonal affective disorder, cardiovascular pathologies, pathologies of the digestive system, insomnia and fatigue due to jetlag, schizophrenia, panic attacks, melancholia, appetite disorders, obesity, psychotic disorders, diabetes, Parkinson's disease, senile dementia, pathologies associated with ageing, migraine, Alzheimer's disease, cerebral circulation disorders, sexual dysfunctions, and cancer, comprising the step of administering to the living body an amount of a compound of claim 1 which is effective for alleviation of said condition.

6. A pharmaceutical composition comprising as active principle an effective amount of a compound as claimed in claim 1, together with one or more pharmaceutically acceptable excipients or vehicles.

* * * * *